United States Patent
Lee et al.

(10) Patent No.: US 8,022,372 B2
(45) Date of Patent: Sep. 20, 2011

(54) APPARATUS AND METHOD FOR BATCH NON-CONTACT MATERIAL CHARACTERIZATION

(75) Inventors: Dong Seung Lee, Bridgewater, NJ (US); Mikhail Belousov, Plainsboro, NJ (US); Eric A. Armour, Pennington, NJ (US); William E. Quinn, Whitehouse Station, NJ (US)

(73) Assignee: Veeco Instruments Inc., Plainview, NY (US)

( * ) Notice: Subject to any disclaimer, the term of this patent is extended or adjusted under 35 U.S.C. 154(b) by 159 days.

(21) Appl. No.: 12/370,044

(22) Filed: Feb. 12, 2009

(65) Prior Publication Data
US 2009/0224175 A1    Sep. 10, 2009

Related U.S. Application Data

(60) Provisional application No. 61/066,074, filed on Feb. 15, 2008.

(51) Int. Cl.
*G01N 21/64* (2006.01)
(52) U.S. Cl. ......... 250/458.1; 250/459.1; 438/7; 438/16
(58) Field of Classification Search ................ 438/7, 16; 250/458.1, 459.1
See application file for complete search history.

(56) References Cited

U.S. PATENT DOCUMENTS

| | | | | |
|---|---|---|---|---|
| 5,213,985 A | * | 5/1993 | Sandroff et al. | 438/7 |
| 5,282,921 A | * | 2/1994 | Poultney | 438/8 |
| 7,130,762 B2 | | 10/2006 | Hellig et al. | |
| 7,159,599 B2 | | 1/2007 | Verhaverbeke et al. | |
| 2004/0246493 A1 | | 12/2004 | Kim et al. | |
| 2005/0286058 A1 | | 12/2005 | Belousov et al. | |
| 2007/0291816 A1 | | 12/2007 | Volf et al. | |

FOREIGN PATENT DOCUMENTS

| | | |
|---|---|---|
| JP | 2007-005645 A | 1/2007 |
| KR | 2003-0094491 A | 12/2003 |
| KR | 2007-0054453 A | 5/2007 |
| WO | 2009/099776 A1 | 8/2009 |

OTHER PUBLICATIONS

International Search Report, PCT/US2009/001006, dated Aug. 13, 2009.
International Search Report, PCT/US2009/031831, dated Jun. 29, 2009 (corresponding to WO 2009/099776).
U.S. Appl. No. 12/812,222 (U.S. National Stage application corresponding to WO 2009/099776).

* cited by examiner

*Primary Examiner* — Constantine Hannaher
(74) *Attorney, Agent, or Firm* — Lerner, David, Littenberg, Krumholz & Mentlik, LLP

(57) ABSTRACT

An apparatus for performing non-contact material characterization includes a wafer carrier adapted to hold a plurality of substrates and a material characterization device, such as a device for performing photoluminescence spectroscopy. The apparatus is adapted to perform non-contact material characterization on at least a portion of the wafer carrier, including the substrates disposed thereon.

34 Claims, 3 Drawing Sheets

APPARATUS AND METHOD FOR BATCH NON-CONTACT MATERIAL CHARACTERIZATION

CROSS-REFERENCE TO RELATED APPLICATIONS

This application claims the benefit of the filing date of U.S. Provisional Patent Application No. 61/066,074 filed Feb. 15, 2008, the disclosure of which is hereby incorporated herein by reference.

BACKGROUND OF THE INVENTION

Various non-contact material characterization techniques are known and are commonly used to measure semiconductor wafers. Non-contact material characterization techniques include: X-ray diffraction ("XRD"), eddy current measurements, and photoluminescence spectroscopy, among others. Photoluminescence spectroscopy, for example, is a technique wherein light is directed from a pump beam onto a sample, such as a semiconductor wafer. Such light may first be absorbed by the material and then dissipated, such as through emission of light (also known as "luminescence"). By measuring the intensity and spectral content of the luminescence by means of collection optics, various important material properties may be gleaned. Such properties revealed by photoluminescence include: determination of band gap, material quality (including the concentration of impurities and defects), composition of the different semiconductor layers, among many other properties. One useful way of analyzing the data may include plotting photoluminescence intensity as a function of wavelength. The full width at half maximum ("FWHM") may then be measured and plotted.

Currently, such material characterization techniques are performed outside of the epitaxial growth apparatus in which the semiconductor wafers are formed. Commonly, the wafers are removed from the epitaxial growth apparatus and placed into cassettes of wafers. The cassettes are then cycled through, and the non-contact material characterization techniques are conducted on a wafer-by-wafer basis, with one wafer being tested at a time. This process can take a considerable amount of time.

Further adding to current processing times is the fact that typical processing apparatuses utilize a chamber referred to as a "load lock" in addition to the principal process chamber. A substrate, or a wafer carrier holding numerous substrates, is inserted into the load lock and brought to equilibrium with an inert atmosphere in the load lock compatible with the epitaxial growth process. Once the substrates are at equilibrium with the inert atmosphere in the load lock, a door between the load lock and the process chamber itself is opened, and the substrates are advanced into the process chamber. After processing, the substrates are removed from the process chamber through the load lock. Multiple handling into and out of the epitaxial growth apparatus takes considerable time, which in turn, slows the process.

With regard to photoluminescence techniques, for example, the wafers are typically placed on a stage and the pump beam and collection optics are either moved in a raster-scan or an outwardly spiraling pattern. That is, in the case of a raster-scan, the pump beam and collection optics are moved linearly across the surface in a first direction from one end of the wafer to the other. After fully scanning a first line across the wafer, the pump beam and collection optics are moved a small, incremental distance perpendicular to the first direction, and then they proceed to linearly scan across the surface parallel to and adjacent to the first line. This process is repeated until the entire surface of the wafer has been scanned. This technique is analogous to, for example, reading lines of text across the surface of a page from left to right and incrementally moving from the top line to the bottom. In the case of an outwardly spiraling pattern, however, the pump beam and collection optics begin scanning at the center of the wafer, and then they proceed to spiral outwardly from the center until the entire surface of the wafer has been scanned.

The above described prior art method of performing non-contact material characterization techniques can be very inefficient. Particularly in the case where multiple processes are to be performed on a group of semiconductor wafers, with material characterization occurring between each process, it can take a substantial amount of time to complete the overall process. Specifically, it can be very time consuming to first remove all of the wafers from the epitaxial growth apparatus after one process is completed, then to perform the testing on each wafer one at a time, and then to reseat the wafers on a wafer carrier and introduce the wafers to the same or a different apparatus for further processing.

BRIEF SUMMARY OF THE INVENTION

One aspect of the present invention provides an apparatus for performing non-contact material characterization on substrates. The apparatus in accordance with this aspect of the invention desirably includes a wafer carrier and a non-contact material characterization device. The wafer carrier desirably has a top surface constructed and arranged to hold at least one substrate thereon. The non-contact material characterization device is desirably constructed and arranged to perform a non-contact material characterization technique on at least a portion of at least one substrate held on the wafer carrier.

The apparatus may further include an epitaxial growth apparatus having a load lock. The non-contact material characterization device is desirably constructed and arranged to perform the non-contact material characterization technique while the wafer carrier is disposed within the load lock of the epitaxial growth apparatus.

A computational device may be connected to the non-contact material characterization device and connected to an epitaxial growth apparatus. The computational device is preferably constructed and arranged to process data from the non-contact material characterization device. Further, the computational device may be operative to adjust conditions in the epitaxial growth apparatus based on the data processed by the computational device.

The non-contact material characterization device may comprise a device for performing photoluminescence spectroscopy.

Still other aspects of the present invention provide methods for performing non-contact material characterization on substrates.

DETAILED DESCRIPTION

Figure 1:
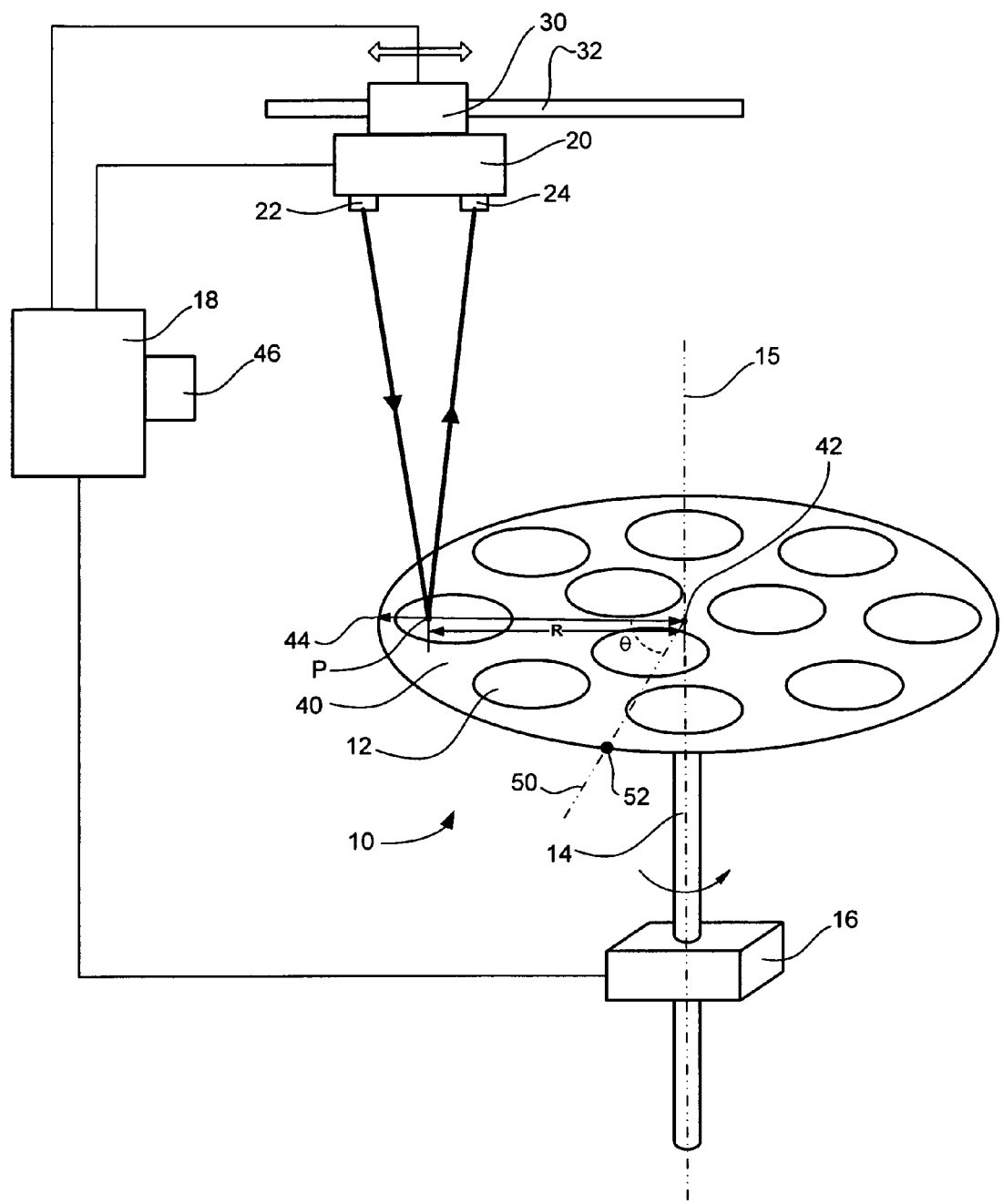
FIG. 1 is a schematic diagram of an apparatus in accordance with one embodiment of the invention.

In describing the preferred embodiments of the invention illustrated in the appended drawings, in which like reference numerals represent like elements, specific terminology will be used for the sake of clarity. However, the invention is not intended to be limited to the specific terms so selected, and it is to be understood that each specific term includes all technical equivalents that operate in a similar manner to accomplish a similar purpose.

An apparatus in accordance with one embodiment of the invention is illustrated in FIG. 1. A wafer carrier 10 is shown holding a plurality of substrates, such as wafers 12. The wafers 12 are preferably held by structures such as pockets (not shown). The wafer carrier 10 is preferably generally circular in shape, although this is not required, and the carrier 10 is preferably composed of a material such as graphite.

The wafer carrier 10 is shown mounted on a spindle 14, which may rotate about axis 15 under the influence of a rotation control device, such as motor 16. The motor 16 is preferably connected to a control device 18, which will be discussed in detail below. The motor 16 is preferably adapted to precisely control the angular position and rotational velocity of the wafer carrier 10. Useful motors 16 for this application may include stepper motors and servos, for example.

The connection (not shown) between the spindle 14 and the wafer carrier 10 is designed so that the wafer carrier 10 may releasably mate with the spindle 14. The connection is preferably configured so that the wafer carrier 10 may be secured to the spindle 14 in such a way that the wafer carrier 10 and spindle 14 may rotate in a fixed angular relationship. The connection is also preferably configured to allow the wafer carrier 10 to be easily detached from the spindle 14, so that the wafer carrier 10 can be moved.

Figure 2:
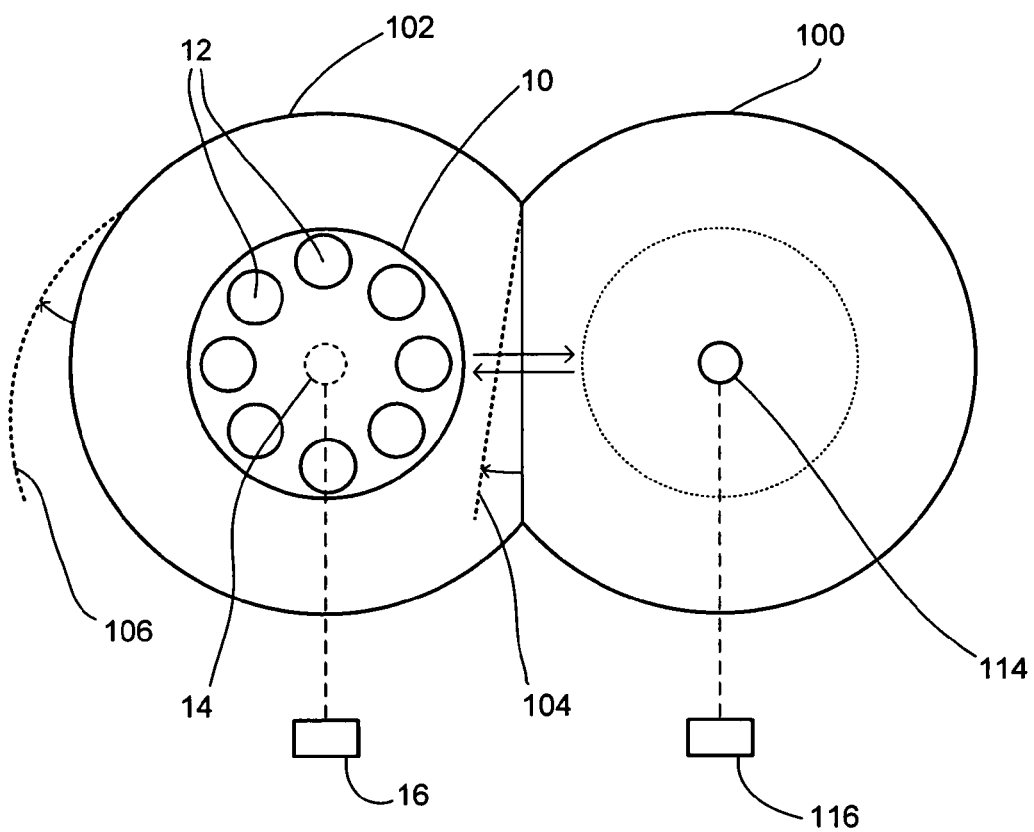
FIG. 2 is a schematic diagram of an epitaxial growth apparatus and load lock in conjunction with an apparatus in accordance with one embodiment of the invention.

As schematically shown in FIG. 2, the wafer carrier 10 is shown in the load lock 102 of an epitaxial growth chamber 100. The load lock 102 is equipped with a chamber door 104 and an exterior door 106. When the chamber door 104 is opened, the interior space within load lock 102 communicates with the interior space of the epitaxial growth chamber 100. When door 104 is closed, the load lock 102 is isolated from the epitaxial growth chamber 100. When door 106 is open, the load lock 102 is open to the exterior of the apparatus, and most typically, is open to room air. The interior space within load lock 102 is connected to a source of a substantially inert gas, so that the interior space within the load lock 102 may be maintained under an atmosphere of the substantially inert gas. As used in this disclosure, the term "substantially inert gas" refers to a gas which does not cause substantial, detrimental reactions with the substrates or layers disposed on the substrates under the conditions prevailing in the load lock. Merely by way of example, for typical substrates carrying layers of III-V semiconductors, gases such as nitrogen, hydrogen, group VIII noble gases, and the like, and mixtures of these gases can be employed.

A conveyor (not shown) may be provided within the load lock 102, the conveyor being configured to move the wafer carrier 10 into or out of the epitaxial growth chamber 100 while the chamber door 104 is open. The conveyor may include any type of mechanical element capable of manipulating the wafer carrier 10, such as, for example, robotic arms, linear slides, pick-and-place mechanisms, mobile chains or belts, or combinations of these elements.

During a preferred use of the apparatus of the present invention, the following steps are carried out in order to perform a non-contact material characterization technique on the wafers 12. After one cycle of epitaxial growth processing is completed on the wafers 12, the door 104 is opened and the wafer carrier 10 is detached from spindle 116. The carrier 10 is then moved from the epitaxial growth chamber 100 into the load lock 102 by the conveyor. The carrier 10 is then mated to the spindle 16. While the wafer carrier 10 is thus disposed within the load lock 102, at least one non-contact material characterization technique is performed, as described in detail below.

It is to be noted that by performing non-contact material characterization measurements while the wafer carrier 10 is in the load lock 102, overall processing time for the substrates will preferably be reduced. Specifically, the amount of time required to move the carrier 10 into and out of the load lock 102 through door 106 in order to perform tests on the substrates is eliminated. Also eliminated is the additional time required allow the atmosphere in the load lock 102 to reach equilibrium, since the wafer carrier 10 is not required to be removed from the load lock 102 during testing and the exterior door 106 is not required to be opened.

A further benefit of performing the material characterization technique in the load lock 102 is the fact that information gathered from the testing can be used to control one or more of the processes. For example, the information gathered can be processed by a programmed computational device integrated with the epitaxial growth apparatus. The computational device may be connected to or incorporated with the control device 18. The computational device is preferably integrated with the epitaxial growth apparatus in such a way that, based on the information gathered by the computational device, the conditions in the growth chamber 100 may be adjusted to optimize the conditions for a subsequent set of substrates. Alternatively or additionally, the computational device may use the information obtained by the non-contact measurement to adjust the process to be applied to the substrates on this particular carrier 10 in a subsequent step, as for example, during further treatment in process chamber 100 or in a different process chamber.

In a typical epitaxial growth apparatus, the wafers 12 are first removed from the epitaxial growth apparatus, and then they are tested in a remote lab, after which the data from the testing may be used to optimize the conditions in the growth chamber. The time it takes to perform those steps creates significant "loop delay," as several processes may have been performed in the growth chamber under the previous process conditions before the conditions are modified based on the material characterization tests. In contrast, by performing the material characterization techniques in the load lock 102 and, thus, quickly providing information to control subsequent processes, the apparatus of the present invention reduces any such "loop delay."

The mechanisms for conducting non-contact material characterization in accordance with a preferred embodiment of the invention will now be discussed. Referring again to FIG. 1, shown mounted above the wafer carrier 10 is a non-contact material characterization device, such as, for example, a photoluminescence device 20. The photoluminescence device 20 may include a pump beam emitter 22 and collection optics 24. The pump beam emitter 22 may be configured to project a precisely defined beam of light at the top surface 40 of the wafer carrier 10, so that the light may either reflect back to the collection optics 24 or so that the luminescence of the material at the top surface 40 of the carrier 10 may be measured by the collection optics 24.

The photoluminescence device 20 is preferably configured to precisely control the frequency of the emitted beam of light. Precise control over the various parameters of the photoluminescence system, such as frequency of the emitted light, will preferably make the entire system more accurate. Furthermore, frequency of the light emitted from the pump beam emitter 22 may be varied in order to target different layers of the semiconductor for analysis. That is, because different layers in a semiconductor having different band gaps will absorb different frequencies of light, the different layers of the semiconductor may be targeted for analysis by selecting the appropriate frequency of light to be absorbed by that layer.

The photoluminescence device 20 as described above is per se a conventional device.

The device 20, in accordance with a preferred embodiment of the present invention, is preferably mounted to a translation mechanism 30 which operates to translate the photoluminescence device 20 along a guiding apparatus, such as a guiding rail 32. The translation mechanism 30 may comprise any known mechanism for translating a device in at least one dimension. Appropriate translation mechanisms 30 may include, for example, linear actuators, belt drives, screw drives, etc.

The translation mechanism 30 and guiding rail 32 are preferably arranged so that the photoluminescence device 20 may scan at least a portion of the wafer carrier 10. In the embodiment illustrated in FIG. 1, the translation mechanism 30 and guiding rail 32 are arranged so that the photoluminescence device 20 may translate back and forth in one dimension across the top surface 40 of the wafer carrier 10. Specifically, in the illustrated embodiment, the photoluminescence device 20 preferably scans the top surface 40 radially with respect to axis 15, moving between the center 42 and the outer edge 44 of the wafer carrier 10. In this way, the device 20 may scan the entire top surface 40 of the wafer carrier 10. That is, the photoluminescence device 20 may scan a line across the top surface 40 from, for example, the center 42 of the wafer carrier 10 in a radial direction to the edge 44. Once the device 20 reaches the edge 44, the motor 16 preferably rotates the wafer carrier 10 about axis 15 by a small degree increment. The device 20 then scans again, for example, from the edge 44 to the center 42. This process is repeated, with the position of the wafer carrier 10 being incrementally rotated with each pass of the photoluminescence device 20 until a complete revolution of the wafer carrier 10 has been made.

During the above-described movement of the photoluminescence device, while the pump beam emitter 22 projects light at the top surface 40 of the wafer carrier 10, the collection optics 24 measure the luminescence of the target portion of the material. The information received by the collection optics 24 may include data such as intensity and wavelength of the collected light. This data is collected as a series of samples representing the measured values of each variable corresponding to each discrete sampled location on the top surface 40 of the wafer carrier 10. By taking samples at many discrete locations (which are very close to each other), the entire top surface 40 of the wafer carrier 10, including the top surfaces of the wafers 12, may be accurately mapped.

The data collected from the photoluminescence device 20 is preferably stored in a memory device 46, which may be a component of the control device 18. The data is preferably associated with the geometrical position of each sampled point P. The position of each point P may be described in many ways, such as Cartesian coordinates. In one embodiment, however, the location of each sample point P may be described by that point's radial coordinates about axis 15. In order to define radial coordinates, the wafer carrier 10 preferably has a reference axis 50 extending from the center 42 of the wafer carrier 10. Thus, each point P may be defined by its radial distance R from the center 42 of the wafer carrier 10 and by its angle $\theta$ from the reference axis 50.

After completing a scan of the wafer carrier 10, the memory device 46 will preferably have all of the photoluminescence data regarding the top surface 40. The memory device 46 also preferably contains information regarding the geometry of the wafer carrier 10, including the relationships of the pockets (which hold the wafers 12) to reference axis 50 and the radial distances of such pockets from center 42. From this data, information regarding each semiconductor wafer 12 may be calculated. That is, by coordinating the input data with its corresponding radial coordinates, and by comparing the coordinates to stored information regarding the geometry of the wafer carrier 10, the control device 18 may correctly link the data from each photoluminescence measurement with the appropriate wafer 12 and with a particular location on the wafer 12.

In this embodiment of the apparatus of the present invention, a control device 18 is designed to fully operate all components of the apparatus. That is, the control device 18 may be adapted to control the movement of the motor 16. The control device 18 is also preferably configured to control the movement of the photoluminescence device 20, by providing appropriate signals to the translation mechanism 30. Further, the control device 18 preferably controls the photoluminescence device 20 itself, including the pump beam emitter 22, and the intensity and frequency of the light emitted therefrom. The control device 18 also preferably receives and processes the input from the collection optics 24, as described above. The control device 18 may include a programmed general purpose computer or a portion of such a computer, or may include plural computational elements physically separate from one another but connected to one another.

The apparatus as described above will preferably speed up the overall processing time for substrates, such as semiconductor wafers 12. In addition to eliminating the time required to remove the wafers 12 from the load lock 102 for testing, as described above, the apparatus of the present invention may further increase efficiency by processing multiple wafers 12 in batches. That is, the apparatus is preferably constructed to scan the entire top surface 40 of a wafer carrier 10 holding many wafers 12, rather than scanning each wafer 12 one at a time.

Many alternatives to the preferred embodiment are encompassed by the present invention, not all of which are described herein. For example, though the above-described reference axis 50 is preferably one defined by the motor 16, in an alternative embodiment there may be a rotary encoder (not shown) connected to the spindle 14, which provides data to the control device 18 regarding the angle $\theta$. Alternatively, a physical axis or mark 52 on the top surface 40 of the wafer carrier 10 may define the axis 50. Such mark 52 is preferably observable by the photoluminescence device 20, such as by constructing it of a material having known photoluminescent properties. In that way, the control device 18 may be able to deduce the radial orientation of the wafer carrier 10 after completing the full scan of the surface 40 and aligning the data with the observed reference axis 50. In a further alternative, no physical mark 52 need be present, and the geometry of the top surface 40 of the wafer carrier 10 may be rotationally asymmetric, such as, for example, by having at least one gap between the wafer pockets be larger than the others. In this embodiment, the data from the complete scan of the top surface 40 may be compared to known information about the geometry of the wafer carrier 10, and the control device 18 may accordingly deduce the rotational coordinates of each sample point P and assign the correct data to the appropriate wafers 12. By constructing the wafer carrier 10 of material having no photoluminescent properties, the control device 18 will be able to distinguish between the wafers 12 and the carrier 10, and the device 28 will be able to assign the correct data to the appropriate wafers 12 accordingly.

Further, the present invention is not limited to the above-described manner of scanning the surface 40 of the wafer carrier 10. Alternative methods may be employed consistent with the present invention. For example, the photoluminescence device 20 may scan the surface 40 by scanning in concentric circles. For instance, the beam from the photoluminescence device 20 may start at the center 42 of the wafer carrier 10 and step out one increment in a radial direction. The device 20 may then scan while the motor 16 fully rotates the wafer carrier 10 once about axis 15. The device 20 may then step out again and the carrier 10 may be rotated once again. This process may be continued until the entire top surface has been scanned. In a similar alternative, the device 20 may perform an outwardly spiraling scan by gradually moving radially outwardly from the center 42 while the wafer carrier 10 continuously rotates.

In a further alternative embodiment, the translation mechanism 30 and guiding rail 32 may be arranged so that the photoluminescence device 20 may translate in two dimensions across the top surface 40 of the wafer carrier 10. For instance, the guiding rail 32 may be mounted on another device, such as a second guiding rail (not shown), which is configured to translate along an axis perpendicular to the guiding rail 32. In accordance with such an embodiment of the invention, the wafer carrier 10 may be scanned by, for example, moving the photoluminescence device 20 in a raster-scan, an outwardly spiraling pattern, or a concentric circle pattern, as described above, over the entire top surface 40 of the carrier 10.

In a further alternative embodiment, the translation mechanism 30 may be replaced by a different means for moving a beam of radiant energy across the surface of the wafer carrier, such as a pivoting mechanism, which may move the beam of light around by pivoting in one or two dimensions.

It is to be further noted that the present invention is not limited to locating the non-contact material characterization device, such as the photoluminescence device 20, in a position directly above the wafer carrier 10. Alternative arrangements of the device 20 may be used. For example, a mirror or other optical device may be attached to the translating mechanism 30 instead of the photoluminescence device 20. In such an embodiment, the photoluminescence device 20 may be disposed in a location remote from the optical device, where it may be configured to project the beam of light towards and receive the reflected light back from the optical device. The optical device may then redirect such beams of light towards the top surface 40 of the wafer carrier 10. Then, by translating the optical device in the manner described above with respect to the photoluminescence device 20, the top surface 40 of the wafer carrier 10 may be similarly scanned without requiring the photoluminescence device 20 itself to be translated. Such optical device may similarly pivot instead of translating, as described above.

In a further alternative, an apparatus in accordance with the present invention need not be incorporated with load lock 102. Instead, the apparatus may be located in and incorporated with a transfer chamber, such as that shown and described in U.S. Provisional Application No. 61/066,031 filed Feb. 15, 2008, and entitled "Cluster Tool and Process for III-V Materials" [hereinafter "the Cluster Tool application"], the entire disclosure of which is fully incorporated by reference herein. The transfer chamber of the Cluster Tool application is a chamber in communication with a plurality of adjacent process chambers. As described in such application, such a configuration may be beneficially used where multiple different processes, each having different process chambers, are to be performed on a substrate. In order to speed up the overall process time on such substrate, the transfer chamber may be adapted to provide an inert atmosphere through which the substrate may be transferred from one process chamber to another. In accordance with the present invention, it may further speed up the overall process time on the substrate to incorporate the apparatus of the present invention into such transfer chamber, where it may be configured to perform non-contact material characterization on the wafer carrier 10 while it is located in the transfer chamber.

Figure 3:
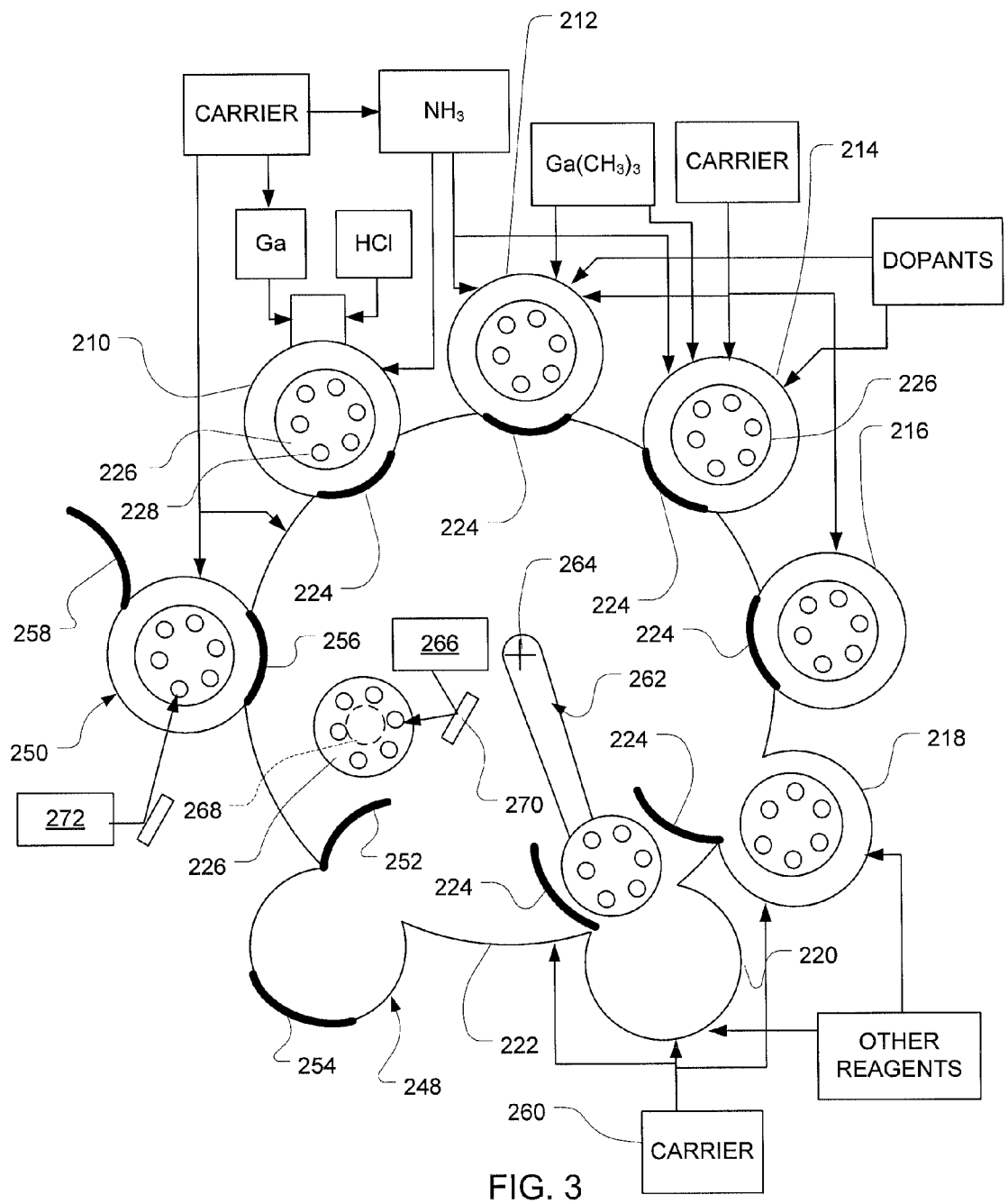
FIG. 3 is a schematic diagram of a transfer chamber in accordance with one embodiment of the invention.

An example of such a transfer chamber is shown in FIG. 3, which illustrates a plurality of processing chambers 210, 212, 214, 216, 218, and 220, and a transfer chamber 222. The processing chambers 210-220 are physically connected to the transfer chamber 222 so that the interior space within each processing chamber can communicate with the transfer chamber. Each processing chamber 210-220 is equipped with a door 224 arranged to selectively permit or block such communication. For example, in the condition depicted in FIG. 3, the doors 224 associated with chambers 210, 212, 214, and 216 are in their respective closed positions, whereas the doors 224 associated with chambers 218 and 220 are in their open positions so that the interior spaces within chambers 218 and 220 are in communication with the interior of transfer chamber 222. Each processing chamber is arranged to receive a carrier 226 holding a plurality of growth substrates 228 such as flat wafers of a crystalline material, and to perform a process on the substrates while the substrates are disposed within the processing chamber. The individual processing chambers are arranged to perform different processes. For example, chamber 210 is arranged to perform a hydride vapor phase epitaxial growth process (referred to herein as "HVPE"), process chambers 212 and 214 are arranged for MOCVD, and additional reaction chambers 216, 218, and 220 are equipped to perform other processes. Merely by way of example, these other processes may include deposition of metals to serve as conductors; epitaxial growth by processes such as molecular beam epitaxy, atomic layer epitaxy, or the like; etching of the substrates or of layers deposited on the substrates; or any other process which can be applied to a substrate, with or without compound semiconductor thereon. Each such chamber desirably is optimized for the particular process or processes to be performed therein.

The apparatus also includes load locks 248 and 250. Load lock 248 is equipped with a transfer chamber door 252 and an exterior door 254. Load lock 250 is equipped with a similar transfer chamber door 256 and exterior door 258. The interior space within transfer chamber 222 is connected to a source 260 of a substantially inert gas, so that the interior space within the transfer chamber 222 may be maintained under an atmosphere of the substantially inert gas. The substantially inert gas may be the same as, or different from, the carrier gases employed in one or more of the reaction chambers, and hence source 260 may be combined with one or more of the other carrier gas sources. Load locks 248 and 250 desirably are also connected a source of a substantially inert gas, which may be the same source 260 or a different source.

A conveyor 262 is also provided within transfer chamber 222. The conveyor is schematically depicted in FIG. 1 as an arm capable of moving in circumferential directions around a central axis 264 and radial directions towards and away from the axis. In other embodiments, the conveyor may include any type of mechanical element capable of manipulating carriers 226, as for example, elements such as linear slides, pick-and-place mechanisms, mobile chains or belts, or combinations of these elements. Also, the circular shape of transfer chamber 222 depicted in FIG. 3 is merely illustrative. Conveyor 262 is arranged so that it can move wafer carriers into or out of any of the process chambers 210-220 while the associated doors 224 of these chambers are open. The conveyor also can move wafer carriers into or out of load locks 248 and 250 when doors 252 and 256 are open. The conveyor is arranged so that it can transfer carriers 226 between the various chambers, as for example, out of either of the load locks into any of the process chambers, or out of any of the process chambers into any other process chamber or into any of the load locks. Conveyor 262 may be arranged to move every wafer in the same sequence, so that every wafer carrier will be moved through the same set of process chambers in the same order. More preferably, however, conveyor 262 is controlled by a programmable or selectively operable mechanism, as for example, one or more electrical, mechanical, or hydraulic components linked to one or more programmable controllers, so that the sequence of movements between chambers can be varied, either for different process runs or for individual wafers within a process run.

The transfer chamber also may be provided with one or more non-contact material characterization devices 266, arranged to direct one or more beams of radiant energy to or through substrates 228 held on a carrier 226 while the carrier is disposed within the transfer chamber, and to monitor one or more properties of the substrates or materials deposited on the substrates based on interactions between the radiant energy and the substrate. The transfer chamber may be equipped with a stand schematically depicted at 268 in FIG. 3 for holding a wafer carrier 226 with substrates 228 thereon, and apparatus for moving the beam from the non-contact material characterization device 266, the substrates, or both, so that the substrates move relative to the beam, and the beam passes over different areas of the various substrates held on a carrier 226. The movement apparatus may include, for example, a support linked to a mechanical motion apparatus which can rotate the support 268, and hence, the wafer carrier about the axis of the wafer carrier. The movement apparatus may be arranged to translate the wafer carrier in directions transverse to its axis. The movement apparatus also may include apparatus for moving one or more components of the non-contact material characterization device, so as to move the beam of radiant energy. Merely by way of example, the non-contact material characterization device may include a beam-directing element 270 such as a mirror, lens, holographic element, or the like, and the movement apparatus may be arranged to move the beam-directing element 270, so as to move the beam. Where the non-contact material characterization device is arranged to receive radiation from the substrate, as for example, in a photoluminescence measurement, the movement device similarly moves the field of view of the non-contact material characterization device. One or both of the load locks 248, 259 may be equipped with a similar non-contact material characterization apparatus 272.

In a method according to one embodiment of the invention, as the substrates are moved between the chambers, properties of the substrates, or the layers being grown thereon, can be monitored using the non-contact material characterization device 266. The information gathered in this manner can be used to control one or more of the processes. For example, a substrate removed from HVPE process chamber 10 can be conveyed to the stand 268 and monitored using the non-contact material characterization device 266. The information gathered in this process can be used to optimize conditions in the HVPE process chamber 210 for a subsequent set of substrates. Alternatively or additionally, the information obtained by the non-contact material characterization can be used to adjust the process to be applied to the substrates on this particular carrier in a subsequent step, as for example, during treatment in MOCVD process chamber 212.

It is appreciated that various means for moving the beam of radiant energy from the photoluminescence device 20 across the surface 40 of the wafer carrier 10 have been disclosed herein. Such means include the one or two dimensional translation mechanism 30, discussed above, or the alternative pivoting mechanism. Other such means include the movement apparatus described in connection with the transfer chamber 222.

It is to be further noted that, though the above described embodiments of the present invention have been described in combination with a specific non-contact material characterization technique, namely photoluminescence spectroscopy, the present invention is not limited to the use of such technique. Any other non-contact material characterization technique may be used in conjunction with the apparatus of the present invention. For example, non-contact surface curvature measurements may be made by directing a beam of light onto a surface of a wafer 12 and detecting the position of the reflected beam. Such a surface curvature measurement technique is shown and described in, for example, pending U.S. application Ser. No. 11/127,834 ("the '834 application"), filed May 12, 2005, Pub. No. 2005/0286058, and entitled "Method and Apparatus for Measuring the Curvature of Reflective Surfaces," the entire disclosure of which is fully incorporated by reference herein.

The apparatus of the present invention is also not limited to performing non-contact material characterization techniques after a cycle of epitaxial growth processing is completed. The apparatus may also perform a pre-run check of the wafers 12 while the wafer carrier 10 is in the load lock 102, or the transfer chamber, and before the wafer carrier 10 is moved into an epitaxial growth chamber 100 for processing. For example, a non-contact material characterization device in accordance with the present invention may include a deflectometer, which may operate similarly to the non-contact surface curvature measurement apparatus described in the '834 application. Specifically, such deflectometer may direct a beam of light onto a surface of a wafer 12 and detect the position of the reflected beam. If the position of the reflected beam deviates from its expected position, it may indicate that the wafer 12 is not sitting properly on the carrier 10. This may occur, for example, when a particle is underneath the wafer 12 when it is loaded on the wafer carrier 10, and the wafer 12 is not sitting parallel to the carrier 10 as a result. It would be beneficial to obtain this information before processing is conducted on the wafers 12, because non-parallel seating will likely cause non-uniform thermal transfer to the wafers 12 during processing.

Furthermore, it is contemplated that material characterization techniques involving physical contact with the wafers 12 may also be performed consistent with the present invention. For example, the above-described photoluminescence device 20 may be replaced with a device having a probe that is configured to extend to the surface 40 of the wafer carrier 10, where it tests the material in contact therewith. Such device may be mounted to a translation mechanism 30, as described above, which may similarly move the probe so that it may scan the entire surface 40 of the wafer carrier 10.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An apparatus for performing non-contact material characterization on substrates, comprising:
   (a) an epitaxial growth apparatus having a processing chamber for depositing a material on at least one substrate held on a wafer carrier, said epitaxial growth apparatus having an ancillary chamber in communication with said processing chamber and configured to receive said wafer carrier; and
   (b) a photoluminescence device constructed and arranged to perform photoluminescence spectroscopy on the material deposited on the at least one substrate held on said wafer carrier while said wafer carrier is disposed in said ancillary chamber.

2. Apparatus as claimed in claim 1 wherein said ancillary chamber is a load lock.

3. Apparatus as claimed in claim 1 wherein said ancillary chamber is a transfer chamber in communication with a plurality of processing chambers.

4. Apparatus as claimed in claim 1 further comprising a computational device connected to said photoluminescence device and connected to said epitaxial growth apparatus, the computational device being constructed and arranged to process data from said photoluminescence device.

5. Apparatus as claimed in claim 4 wherein the computational device is operative to adjust conditions in said epitaxial growth apparatus based on the data processed by the computational device in order to optimize the conditions for a subsequent set of substrates.

6. Apparatus as claimed in claim 1 wherein said wafer carrier is constructed of a material having substantially no photoluminescent properties.

7. Apparatus as claimed in claim 1 wherein said photoluminescence device is constructed and arranged to direct at least one beam of radiant energy towards said wafer carrier, and further comprising a means for moving the beam of radiant energy across a surface of said wafer carrier.

8. Apparatus as claimed in claim 1 wherein said photoluminescence device is constructed and arranged to direct at least one beam of radiant energy towards said wafer carrier, and further comprising a translation mechanism for moving the beam of radiant energy across a surface of said wafer carrier.

9. Apparatus as claimed in claim 8 wherein the translation mechanism is constructed and arranged to move the beam in one dimension.

10. Apparatus as claimed in claim 8 wherein said wafer carrier has a center and an outer edge, the translation mechanism being constructed and arranged to move the beam between the center and the outer edge.

11. Apparatus as claimed in claim 8 wherein the translation mechanism is constructed and arranged to move the beam in two dimensions.

12. Apparatus as claimed in claim 8 wherein said photoluminescence device is constructed and arranged to perform a raster-scan across the surface of said wafer carrier.

13. Apparatus as claimed in claim 8 wherein said photoluminescence device is constructed and arranged to perform an outwardly spiraling scan across the surface of said wafer carrier.

14. Apparatus as claimed in claim 8 wherein said photoluminescence device is constructed and arranged to perform a concentric circle scan across the surface of said wafer carrier.

15. Apparatus as claimed in claim 1 further comprising a rotation control device connectable to said wafer carrier, the rotation control device being constructed and arranged to rotate said wafer carrier while said wafer carrier is disposed in said ancillary chamber.

16. Apparatus as claimed in claim 1 wherein said photoluminescence device is disposed above said wafer carrier.

17. A method for performing non-contact material characterization on substrates, comprising the steps of:
   (a) positioning a wafer carrier in an ancillary chamber of an epitaxial growth apparatus, said wafer carrier holding at least one substrate thereon, said epitaxial growth apparatus having a processing chamber in communication with said ancillary chamber, said processing chamber being adapted to deposit a material on the at least one substrate held on said wafer carrier;
   (b) performing photoluminescence spectroscopy on the material deposited on the at least one substrate held on the wafer carrier while the wafer carrier is disposed in the ancillary chamber; and
   (c) adjusting conditions in the epitaxial growth apparatus based on information obtained during the step of performing photoluminescence spectroscopy, in order to optimize the conditions for a subsequent set of substrates.

18. A method as claimed in claim 17 wherein said step of performing photoluminescence spectroscopy includes directing at least one beam of radiant energy towards the wafer carrier and moving the beam of radiant energy across a surface of the wafer carrier.

19. A method as claimed in claim 18 wherein the step of moving the beam of radiant energy comprises moving a translating mechanism in one dimension.

20. A method as claimed in claim 18 wherein the wafer carrier has a center and an outer edge, the step of moving the beam of radiant energy comprising moving the beam between the center and the outer edge.

21. A method as claimed in claim 18 wherein the step of moving the beam of radiant energy comprises moving a translating mechanism in two dimensions.

22. A method as claimed in claim 18 wherein the step of moving the beam of radiant energy comprises pivoting the beam of radiant energy.

23. A method as claimed in claim 17 wherein said step of performing photoluminescence spectroscopy includes directing at least one beam of radiant energy towards the wafer carrier and rotating the wafer carrier about a central axis of the carrier.

24. A method as claimed in claim 17 wherein said step of performing photoluminescence spectroscopy includes directing at least one beam of radiant energy towards the wafer carrier and monitoring one or more of the properties of the material deposited on the at least one substrate that is contacted by the at least one beam of radiant energy.

25. A method as claimed in claim 24 further comprising storing the monitored properties in a memory device.

26. A method as claimed in claim 24 further comprising identifying a geometrical coordinate of a location on the wafer carrier contacted by the at least one beam of radiant energy, and further comprising associating the monitored properties with the geometrical coordinate corresponding thereto.

27. A method as claimed in claim 17 further comprising the step of performing an epitaxial process on the at least one substrate on the wafer carrier.

28. A method as claimed in claim 27 further comprising moving the wafer carrier into the ancillary chamber of the epitaxial growth apparatus after said step of performing an epitaxial process.

29. A method as claimed in claim 28 wherein said step of performing photoluminescence spectroscopy further includes monitoring one or more of the properties of the at least one substrate.

30. A method as claimed in claim 28 wherein the ancillary chamber is a transfer chamber connecting multiple epitaxial process chambers.

31. A method as claimed in claim 30 wherein said step of performing photoluminescence spectroscopy further includes monitoring one or more of the properties of the at least one substrate.

32. A method as claimed in claim 31 further comprising the step of adjusting conditions in at least one of the epitaxial process chambers based on the monitored properties in order to adjust a process to be applied to the at least one substrate held on the wafer carrier.

33. A method as claimed in claim 31 further comprising the step of selecting one of the epitaxial process chambers for additional processing based on the monitored properties in order to optimize a process to be applied to the at least one substrate held on the wafer carrier.

34. A method as claimed in claim 28 wherein the ancillary chamber is a load lock.

* * * * *